(12) United States Patent
Horton

(10) Patent No.: US 9,615,907 B2
(45) Date of Patent: Apr. 11, 2017

(54) DEPLOYMENT RODS FOR USE WITH IMPLANTABLE HERNIA PROSTHESES

(71) Applicant: Atrium Medical Corporation, Hudson, NH (US)

(72) Inventor: Anthony R. Horton, Manchester, NH (US)

(73) Assignee: Atrium Medical Corporation, Merrimack, NH (US)

( * ) Notice: Subject to any disclaimer, the term of this patent is extended or adjusted under 35 U.S.C. 154(b) by 732 days.

(21) Appl. No.: 13/829,398

(22) Filed: Mar. 14, 2013

(65) Prior Publication Data

US 2014/0155917 A1    Jun. 5, 2014

Related U.S. Application Data

(60) Provisional application No. 61/731,909, filed on Nov. 30, 2012.

(51) Int. Cl.
*A61B 17/08* (2006.01)
*A61F 2/00* (2006.01)

(52) U.S. Cl.
CPC .... *A61F 2/0063* (2013.01); *A61F 2002/0072* (2013.01)

(58) Field of Classification Search
CPC ................. A61F 2/0063; A61F 2002/0072
See application file for complete search history.

(56) References Cited

U.S. PATENT DOCUMENTS

| 3,421,722 A | * | 1/1969 | May | A63H 27/002 244/155 R |
| 5,366,460 A | | 11/1994 | Eberbach et al. | |
| 5,370,650 A | | 12/1994 | Tovey et al. | |
| (Continued) | | | | |

FOREIGN PATENT DOCUMENTS

| WO | WO 2011/043795 | 4/2011 |
| WO | WO 2011/128903 | 10/2011 |

OTHER PUBLICATIONS

International Search Report for International Application PCT/US2013/034121, dated Jun. 5, 2013.
(Continued)

*Primary Examiner* — Todd J Scherbel
*Assistant Examiner* — Son Dang
(74) *Attorney, Agent, or Firm* — Wesley Scott Ashton

(57) ABSTRACT

An implantable prosthesis device and system for insertion, deployment, and fixation of a hernia prosthesis. The system includes two or more deployment rods removably affixed to the prosthesis. Each rod extends across a majority of a width of the prosthesis and beyond one end of the width of the prosthesis. The rods are arranged generally parallel to one another when in a rolled configuration. The rods are separate, physically noncontiguous wire rods that are not operably coupled to one another. The rods provide structural reinforcement and increased rigidity across the width of the implantable hernia prosthesis while maintaining the ability of the prosthesis to experience bends in its length. In this way, the rods allow a user to separately manipulate discrete portions of the prosthesis while to maintaining the ability of the prosthesis to be rolled up and inserted into the body of a patient through, e.g., a trocar.

26 Claims, 9 Drawing Sheets

(56) References Cited

U.S. PATENT DOCUMENTS

| | | | |
|---|---|---|---|
| 6,319,264 B1 * | 11/2001 | Tormala | A61F 2/0063 |
| | | | 606/151 |
| 6,551,356 B2 | 4/2003 | Rousseau | |
| 6,575,988 B2 | 6/2003 | Rousseau | |
| 6,669,735 B1 | 12/2003 | Pelissier | |
| 6,814,743 B2 | 11/2004 | Chin et al. | |
| 7,101,381 B2 | 9/2006 | Ford et al. | |
| 7,544,203 B2 | 6/2009 | Chin et al. | |
| 7,947,062 B2 | 5/2011 | Chin et al. | |
| 2001/0016754 A1 | 8/2001 | Adams et al. | |
| 2004/0019360 A1 | 1/2004 | Farnsworth et al. | |
| 2005/0043716 A1 | 2/2005 | Frimer | |
| 2007/0299538 A1 | 12/2007 | Roeber | |
| 2008/0147200 A1 | 6/2008 | Rousseau et al. | |
| 2008/0237287 A1 | 10/2008 | Mitchinson | |
| 2009/0082792 A1 | 3/2009 | Koyfman et al. | |
| 2009/0270999 A1 | 10/2009 | Brown | |
| 2009/0326676 A1 | 12/2009 | Dupic et al. | |
| 2011/0040311 A1 | 2/2011 | Levin et al. | |
| 2011/0082479 A1 | 4/2011 | Friedlander | |
| 2011/0144667 A1 | 6/2011 | Horton et al. | |
| 2011/0224704 A1 | 9/2011 | Bailly et al. | |
| 2011/0295283 A1 | 12/2011 | Darois et al. | |
| 2013/0282033 A1 * | 10/2013 | Caballero | A61F 2/0063 |
| | | | 606/151 |

OTHER PUBLICATIONS

International Search Report for International Application PCT/US2013/034107, dated Aug. 6, 2013.
Non-Final Office Action for U.S. Appl. No. 13/829,987, dated Feb. 10, 2014.

* cited by examiner

DEPLOYMENT RODS FOR USE WITH IMPLANTABLE HERNIA PROSTHESES

RELATED APPLICATION

This application claims priority to, and the benefit of, U.S. Provisional Application 61/731,909, filed Nov. 30, 2012, for all subject matter common to both applications. The disclosure of said provisional application is hereby incorporated by reference in its entirety.

FIELD OF THE INVENTION

The present invention relates to deployment devices suitable for use with implantable prostheses used in hernia repair. More particularly, the present invention relates to deployment rods configured to facilitate handling and deployment of implantable hernia prostheses during laparoscopic surgical procedures.

BACKGROUND OF THE INVENTION

In laparoscopic hernia repair, implantable hernia prostheses are utilized to provide reinforcement and support at the hernia defect. Such implantable hernia prostheses or other sheet-like prostheses (e.g., films, surgical fabrics, and the like) are rolled up and inserted (e.g., housed within a trocar cannula) through a small incision cut into the skin and abdominal wall. Generally, such implantable hernia prostheses are flat sheets (e.g., of woven or knitted surgical fabric) that are trimmed to fit the anatomy of the defect site as needed prior to being rolled up and inserted through the incision. Once inserted, the implantable hernia prosthesis can be unrolled and affixed to the defect site using sutures, tacks, or the like. The implantable hernia prosthesis can integrate into the surrounding tissue via tissue ingrowth.

However, manipulating implantable hernia prostheses during laparoscopic procedures presents numerous challenges to a surgeon. For example, trocars only provide a limited range of motion and require the user to grip small instruments such as graspers when manipulating (e.g., unrolling, positioning, etc.) the implantable hernia prosthesis. Moreover, in many instances, the mechanical and physical conditions of many implantable hernia prostheses change upon exposure to bodily conditions and environments, such as bodily temperatures, body fluids, and the like. In particular, when exposed to moisture, such implantable hernia prostheses can hydrate and become less stiff, making them more difficult to deploy or unroll. Additionally, in some instances, the implantable hernia prosthesis may include a tissue separating layer intended to minimize visceral tissue attachment to the prosthesis. Such tissue separating layers can hydrate, warm up, and soften, making them more fragile and prone to tearing, abrasions, or rupture, thereby complicating a user's ability to handle and place the implantable hernia prosthesis during surgery and implantation. Such self-adhering layers can further complicate a user's ability to handle and place the implantable hernia prosthesis during surgery and implantation.

Additionally, in abdominal and pelvic laparoscopic procedures, the insertion, placement, and fixation of such implantable prostheses prove even more challenging. Due to the use of extremely delicate prostheses in such surgical procedures, the aforementioned concerns are magnified by the increased risk of rupture or tear. As such, even routine handling of the extremely delicate prostheses can be associated with risk of failure of the delicate prosthesis in such procedures as currently performed by doctors.

SUMMARY

There is a need in the art for a deployment device that enables the convenient delivery, deployment, and placement of implantable hernia prostheses (e.g., meshes, films, patches, fabrics, etc.). The present invention is directed toward solutions to address this and other needs, in addition to having other desirable characteristics that will be appreciated by one of skill in the art upon reading the present specification.

In accordance with an example embodiment of the present invention, a system is provided. The system can include a prosthesis including a first flexible mesh sheet structure. Two or more elongate rods each can be removably coupled with the prosthesis and each can be more rigid than the mesh sheet structure, in such a way that the combination of the two or more elongate rods with the mesh sheet structure rigidifies the mesh sheet structure along a length of each of the two or more elongate rods. The system can be configured to be rolled in a direction substantially orthogonal to central longitudinal axes of the two or more elongate rods in such a way that all or substantially all of the mesh sheet structure forms one or more rolls without bending the two or more elongate rods.

In accordance with aspects of the present invention, the two or more elongate rods can be separate and distinct from each other and two of the two or more elongate rods can be independently moveable relative to each other. One or more fastening mechanisms can couple the two or more elongate rods to the first mesh sheet structure of the prosthesis. Each one of the two or more elongate rods can be slidable out of the one or more fastening mechanisms in a direction generally along the central longitudinal axis of that one of the two or more elongate rods. The one or more fastening mechanisms can be configured to be cut to release the two or more elongate rods and can be adapted to be removed from the mesh sheet structure. A second flexible mesh sheet structure can be coupled to and can form a layer on the first mesh sheet structure. The two or more elongate rods can be disposed between the first and second mesh sheet layers which removably couple the two or more elongate rods to the sheet in such a way that the two or more elongate rods are slidable out from between the first and second mesh sheet structures. The prosthesis can include a second flexible mesh sheet structure coupled to and forming a layer on the first mesh sheet structure, and each of the two or more elongate rods can be affixed to the first flexible mesh sheet structure or the second flexible mesh sheet structure.

In accordance with yet further aspects of the present invention, at least one of the two or more elongate rods coupled to the prosthesis can extend beyond and exterior to a perimeter edge of the prosthesis. At least one of the two or more elongate rods coupled to the prosthesis can be graspable and maneuverable by a laparoscopic grasper or other separate tool. Each of the two or more elongate rods can extend across a majority of a dimension of the prosthesis. A first of the two or more elongate rods can be disposed at a first end of the prosthesis and a second of the two or more elongate rods is disposed at a second end of the prosthesis, the second end of the prosthesis being opposite the first end. The two or more elongate rods further can include a third rod disposed between the first and second rods at a central portion of the prosthesis. The two or more elongate rods can have a rigidity suitable for using the two or more elongate rods to manipulate and position the prosthesis at a target site (e.g., pushing, pulling, rotating, pivoting, lateral movement, raising, lowering, and the like). Each of the two or more elongate rods can include a wire rod, a plastic rod, or a rod constructed of another material.

In accordance with an example embodiment of the present invention, a method for deploying a mesh prosthesis using a system comprising a prosthesis comprising a first flexible mesh sheet structure, and two or more elongate rods each being removably coupled with the prosthesis and each being more rigid than the mesh sheet structure in such a way that the combination of the two or more elongate rods with the mesh sheet structure rigidifies the mesh sheet structure along a length of each of the two or more elongate rods, is provided. The method can include providing a rolled prosthesis in which, using the two or more elongate rods, the prosthesis is rolled in a direction substantially orthogonal to a central longitudinal axes of the two or more elongate rods in such a way that all or substantially all of the mesh sheet structure forms one or more rolls without bending the two or more elongate rods. The method can continue with inserting the prosthesis into a bodily cavity, unrolling the prosthesis, using the two or more elongate rods, and removing the two or more elongate rods from the prosthesis.

In accordance with aspects of the present invention, wherein the two or more elongate rods can be separate and distinct from each other and two of the two or more elongate rods can be independently moveable relative to each other. One or more fastening mechanisms can be provided coupling the two or more elongate rods to the first mesh sheet structure of the prosthesis.

In accordance with aspects of the present invention, the step of removing the two or more elongate rods can include sliding the two or more elongate rods out of the one or more fastening mechanisms in a direction generally along the central longitudinal axis of each respective rod of the two or more elongate rods.

In accordance with aspects of the present invention, the prosthesis can further include a second flexible mesh sheet structure coupled to and forming a layer on the first mesh sheet structure. The two or more elongate rods are can be disposed between the first and second mesh sheet layers which removably couple the two or more elongate rods to the sheet in such a way that the step of removing the two or more elongate rods can include sliding the two or more elongate rods out from between the first and second mesh sheet structures.

In accordance with aspects of the present invention, at least one of the two or more elongate rods coupled to the prosthesis can extend beyond and exterior to a perimeter edge of the prosthesis. At least one of the two or more elongate rods coupled to the prosthesis can be graspable and maneuverable by a laparoscopic grasper or other separate tool. The two or more elongate rods can have a rigidity suitable for using the two or more elongate rods to manipulate and position the prosthesis at a target site, and the method can further include manipulating and positioning the prosthesis at the target site using the two or more elongate rods.

In accordance with aspects of the present invention, the prosthesis may be rolled at a point of manufacture or may be rolled by a user at the time of performing the deployment method.

In accordance with an example embodiment of the present invention, a system includes a prosthesis having a first flexible mesh sheet structure. Two or more elongate rods can each be removably coupled with the prosthesis and each be more rigid than the mesh sheet structure, in such a way that the combination of the two or more elongate rods with the mesh sheet structure rigidifies the mesh sheet structure along a length of each of the two or more elongate rods. The system can be configured to be rolled in a direction substantially orthogonal to a central longitudinal axes of the two or more elongate rods in such a way that all or substantially all of the mesh sheet structure forms one or more rolls. The two or more elongate rods can be separate and distinct from each other and two of the two or more elongate rods can be independently moveable relative to each other.

In accordance with one example embodiment of the present invention, a system includes a prosthesis having a first flexible mesh sheet structure. Two or more elongate rods can each be removably coupled with the prosthesis and each be more rigid than the mesh sheet structure, in such a way that the combination of the two or more elongate rods with the mesh sheet structure rigidifies the mesh sheet structure along a length of each of the two or more elongate rods. The system can be configured to be rolled in a direction substantially orthogonal to a central longitudinal axes of the two or more elongate rods in such a way that all or substantially all of the mesh sheet structure forms one or more rolls. The two or more elongate rods can be separate and distinct from each other and two of the two or more elongate rods can be independently moveable relative to each other. The two or more elongate rods can have a rigidity suitable for using the two or more elongate rods to manipulate and position the prosthesis at a target site.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
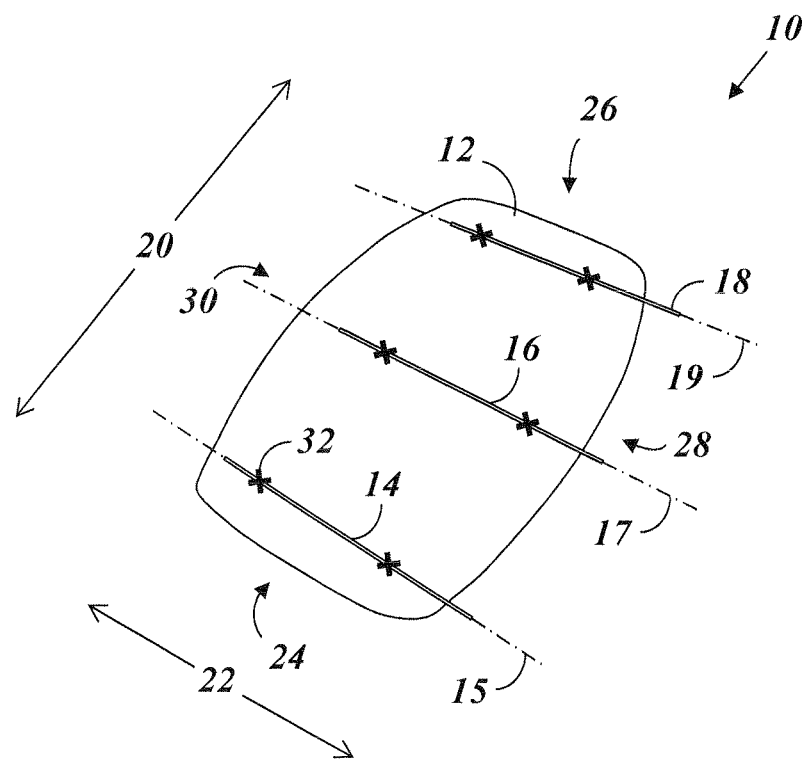
FIG. 1 is a perspective view of a system including an implantable hernia prosthesis and three deployment rods coupled thereto, according to an example embodiment of the present invention.

An illustrative embodiment of the present invention relates to a system for insertion, deployment, and/or fixation of an implantable hernia prosthesis. For example, the implantable hernia prosthesis can include a flexible mesh sheet structure, in singular form, or layered, as would be appreciated by one of skill in the art. In addition to the implantable hernia prosthesis, the system also can include two or more (e.g., three, in an example embodiment described herein) elongate deployment rods removably coupled with the implantable hernia prosthesis. The deployment rods can be substantially rigid relative to the mesh sheet structure. Each of the deployment rods can have a central longitudinal axis, and the system, in particular the implantable hernia prosthesis, can be configured to be rolled in a direction substantially orthogonal to the central longitudinal axes of the two or more deployment rods in such a way that all or substantially all of the implantable hernia prosthesis (e.g., including the mesh sheet structure) forms one or more rolls without bending the two or more elongate rods.

In general, the deployment rods provide the implantable hernia prosthesis with structural reinforcement and increased rigidity along the lengths of the deployment rods, without hindering the ability of the implantable hernia prosthesis to bend orthogonally to the central longitudinal axes of the deployment rods. For example, in one illustrative embodiment, the deployment rods extend across the width of the prosthesis, in such a way as to rigidify the width of the prosthesis without sacrificing the ability of the prosthesis to experience bends in its length. Stated differently, the deployment rods of such an illustrative embodiment increase the rigidity of the implantable hernia prosthesis along the width, but not the length, dimensions as indicated in the figures. Accordingly, as stated previously, the system is capable of being rolled up in a direction substantially orthogonal to the central longitudinal axes of the deployment rods, thereby allowing the system to pass through one or more trocars (e.g., during implantation). It should be noted that the phrase "substantially orthogonal", or "orthogonal", when referring to the direction of roll of the prosthesis around the deployment rods, is intended to capture a direction of roll that is sufficient to result in the prosthesis actually wrapping about the deployment rod substantially overlapping itself without spiraling in one direction or another. Sufficient illustration of this orthogonal arrangement, direction, and movement, are provided in the figures to enable one of skill in the art to appreciate the general nature of the terms and phrases without undue experimentation, such that the present invention is fully enabled.

As described in greater detail herein, the implantable hernia prosthesis can include a mesh sheet structure that is more flexible than the deployment rods. In particular, each of the deployment rods can be an elongate rod that is more rigid than the mesh sheet structure, in such a way that the deployment rods rigidify the mesh sheet structure along a length of each of the deployment rods. Accordingly, the elongate rods can be configured in this way to maintain the shape of the sheet mesh structure (e.g., and of the implantable hernia prosthesis generally) along the central longitudinal axes of the deployment rods. Furthermore, in accordance with in illustrative embodiments of the present invention, the deployment rods can have a rigidity that is sufficiently high to allow the deployment rods to: (a) support the weight of the sheet mesh structure (e.g., and of the implantable hernia prosthesis generally), and (b) serve as tools for manipulating the shape and/or position of the sheet mesh structure (e.g., and of the implantable hernia prosthesis generally) during rolling, insertion, deployment, and placement thereof.

In accordance with an illustrative and non-limiting embodiment of the present invention, the deployment rods are separate, physically noncontiguous, wire rods that are independently movable relative to one another. Furthermore, the deployment rods can be separately removable, in such a way as to enable piecewise deployment and fixation of discrete portions of the implantable hernia prosthesis, as described in greater detail below.

FIGS. 1 through 9, wherein like parts are designated by like reference numerals throughout, illustrate example embodiments of a system for deploying an implantable hernia prosthesis, according to the present invention. Although the present invention will be described with reference to the example embodiments illustrated in the figures, it should be understood that many alternative forms can embody the present invention. For example, although for purposes of clarity the example embodiments are described with reference to an implantable hernia prosthesis, the present invention alternatively can be implemented in accordance with any other suitable prosthesis. Accordingly, the present invention is not limited exclusively to implantable hernia prostheses, as would be appreciated by one of skill in the art upon reading the present specification. One of skill in the art will additionally appreciate a variety of ways to alter the parameters of the embodiments disclosed, such as the size, shape, or type of elements or materials, in a manner still in keeping with the spirit and scope of the present invention. All such alternatives and modifications are contemplated within the scope of the present invention.

Figure 2:
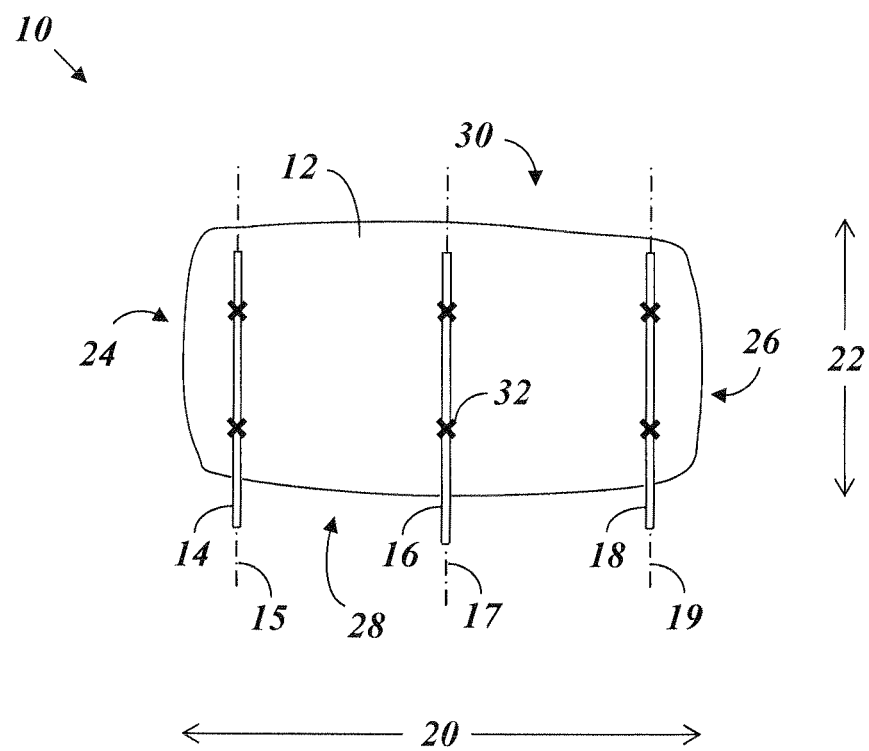
FIG. 2 is a top view of the system of FIG. 1, according to aspects of the present invention.

FIGS. 1 and 2 depict a perspective view and a top view, respectively, of a system 10 for inserting, deploying, and positioning an implantable hernia prosthesis 12, in accordance with an example embodiment of the present invention. As shown in the example embodiment of FIGS. 1 and 2, the implantable hernia prosthesis 12 includes a generally flat, flexible sheet of mesh, as would be appreciated by one of skill in the art. More specifically, in the example embodiment of FIGS. 1 and 2, the implantable hernia prosthesis 12 is constructed of a single layer of a polypropylene filament knitted mesh. Examples of polypropylene meshes suitable for use with the present invention include, but are not limited to, C-QUR™ Mesh, C-QUR™ Mosaic Mesh, C-QUR™ Film, C-QUR FX™ Mesh, ProLite™ and ProLite Ultra™, all manufactured by Atrium Medical Corporation of Hudson, N.H. Additional meshes manufactured by other sources are also suitable for use with the present invention, as would be appreciated by one of skill in the art.

The implantable hernia prosthesis 12 has a length 20 and a width 22. The length 20 may be greater than the width 22, as illustrated in FIGS. 1 and 2. Alternatively, in some embodiments, the width 22 is greater than the length 20. In yet other embodiments, the length 20 and the width 22 are equal in magnitude. The implantable hernia prosthesis 12 generally is sized and shaped to have a surface area that is larger than that of a hernia (or other bodily defect). In this way, the implantable hernia prosthesis 12 can be sized, shaped, and dimensioned to completely cover the hole or defect upon implantation and proper placement at the defect site. As stated previously herein, the implantable hernia prosthesis 12 generally is flexible, as would be appreciated by one of skill in the art. In particular, the implantable hernia prosthesis 12 generally is capable of being rolled up into a single-roll configuration or a double-roll configuration, e.g., prior to implantation during use thereof.

The implantable hernia prosthesis 12 may be uncoated or may include a coating. For embodiments of the present invention in which the implantable hernia prosthesis 12 includes a coating, the coating may be any suitable coating, including as a non-limiting example a hydrolysable bioabsorbable cross-linked fatty acid based material that includes a partially or fully cured fish oil or omega-3 fatty acid. Such a coating can be applied to the implantable hernia prosthesis 12 with sufficient thickness to serve as a physical protective layer between surrounding tissue and the surface of the implantable hernia prosthesis 12. Additionally, the hernia prosthesis 12 is preferably sterilized by a suitable sterilization process such as e-beam, cobalt 60 gamma irradiation, and ethylene oxide gas.

In addition to the implantable hernia prosthesis 12, the system 10 of FIGS. 1 and 2 also includes two or more elongate deployment rods configured to facilitate insertion, placement, deployment, and fixation of the implantable hernia prosthesis 12. In the example embodiment of FIGS. 1 and 2, the system 10 includes a first deployment rod 14, a second deployment rod 16, and a third deployment rod 18. In the example embodiment of FIGS. 1 and 2, each of the deployment rods 14, 16, 18 is a substantially straight (e.g., non-curved), elongate rod having a length that extends across at least a majority of the width 22 of the implantable hernia prosthesis 12. In some embodiments, the deployment rods 14, 16, 18 have a flexibility sufficient to enable the deployment rods 14, 16, 18 to bend and conform to the contour of the shape of the abdominal wall or other hernia defect site, while still being more rigid than the mesh hernia prosthesis 12. In the example embodiment of FIGS. 1 and 2, each of the deployment rods 14, 16, 18 extends across substantially all of the width 22 of the implantable hernia prosthesis 12. The deployment rods 14, 16, 18 can be generally cylindrical in shape (as shown in FIGS. 1 and 2), or can have a shape generally resembling a rectangular prism, triangular pyramid, or any other suitable shape, as would be appreciated by those of skill in the art. The deployment rods 14, 16, 18 can be tapered at one or both of their ends. In the example embodiment of FIGS. 1 and 2, the deployment rods 14, 16, 18 are arranged substantially parallel to one another, as depicted. The phrase "substantially parallel" as utilized herein is intended to have the ordinary meaning as would be understood by those of skill in the art. In particular, the underlying motivation for the deployment rods 14, 16, 18 to be arranged "substantially parallel" is so that when the prosthesis is rolled as described herein, the deployment rods 14, 16, 18 are in sufficient parallel alignment with each other so as to not hinder or interfere in the rolling process in a way such that either (i) the rolling process becomes unduly difficult or impossible as a result of such interference and/or the prosthesis; or (ii) limits the ability for the rolled prosthesis to accommodate a size (e.g., maximum diameter when rolled) sufficient for its intended usage (e.g., to fit through a trocar port). As noted in a later described embodiment, the substantially parallel arrangement of the deployment rods 14, 16, 18 can result upon rolling the prosthesis and not when the prosthesis is flat (e.g., see FIG. 5 and corresponding description).

Each of the deployment rods 14, 16, 18 extends beyond an edge of the implantable hernia prosthesis 12. Specifically, in the example embodiment of FIGS. 1 and 2, each of the deployment rods 14, 16, 18 extends beyond the same end 28 of the width 22 of the implantable hernia prosthesis 12. Furthermore, in the example embodiment of FIGS. 1 and 2, the deployment rods 14, 16, 18 do not extend beyond the opposite end 30 of the width 22 of the implantable hernia prosthesis 12.

With embodiments such as depicted in FIGS. 1 and 2, it should be appreciated that the deployment rods 14, 16, 18 can extend beyond the end 28 of the width 22 of the implantable hernia prosthesis 12 in the same amount or in differing amounts. Furthermore, the deployment rods 14, 16, 18 can span or occupy the same amount or different amounts of the width 22 of the implantable hernia prosthesis 12. In some alternative embodiments, one, some, or all of the deployment rods 14, 16, 18 extend beyond two opposite edges of the implantable hernia prosthesis 12 (e.g., extend beyond both ends 28, 30 of the width 22 of the implantable hernia prosthesis 12).

In the example embodiment of FIGS. 1 and 2, the first deployment rod 14 is positioned proximate a first end 24 of the length 20 of the implantable hernia prosthesis 12 and spaced inward from the first end 24 of the length 20 (e.g., by a small amount relative to the full length 20, as would be appreciated by one of skill in the art upon reading the present specification). The second deployment rod 16 is positioned proximate or at a center or midpoint of the length 20 of the implantable hernia prosthesis 12. The third deployment rod 18 is positioned proximate a second end 26 of the length 20 of the implantable hernia prosthesis 12 that is opposite the first end 24 of the length 20 of the implantable hernia prosthesis 12. The third deployment rod 18 is spaced inward from the second end 26 of the length 20 of the implantable hernia prosthesis 12, e.g., by a small amount relative to the full length 20 of the implantable hernia prosthesis 12, as would be appreciated by one of skill in the art upon reading the present specification. Accordingly, as shown in FIGS. 1 and 2, the deployment rods 14, 16, 18 can be separate and noncontiguous with one another (e.g., not in physical contact with one another) when the implantable hernia prosthesis 12 is in the unrolled, substantially flat configuration. Furthermore, in accordance with illustrative embodiments of the present invention, the deployment rods 14, 16, 18 are not operably connected to one another (e.g., by support bars, etc.). Thus, the two outer deployment rods 14, 18 are independently movable within a range of motion. Stated differently, each one of the two outer deployment rods 14, 18 has a range of motion through which movement of the deployment rod 14, 18 along a given distance does not have an affect on movement of the other of the two outer deployment rods 14, 18.

The deployment rods 14, 16, 18 can be spaced apart from one another along the length 20 of the implantable hernia prosthesis 12, e.g., can be spaced apart in equal amounts as depicted in FIGS. 1 and 2. Alternatively, the deployment rods 14, 16, 18 can be separated by non-equal amounts. The positions of the deployment rods 14, 16, 18 depicted and described herein are illustrative and in no way limit the present invention. In general, the deployment rods 14, 16, 18 can be disposed at any suitable positions allowing the deployment rods 14, 16, 18 to aid in the handling of the implantable hernia prosthesis 12 (e.g., during insertion, deployment, placement, and the like).

The deployment rods 14, 16, 18 are removably coupled with the implantable hernia prosthesis 12. In illustrative embodiments, the deployment rods 14, 16, 18 are coupled with the implantable hernia prosthesis 12 independently of one another. Stated differently, the coupling of one of the deployment rods 14, 16, 18 does not depend upon the coupling of any other of the deployment rods 14, 16, 18. For example, separate and distinct fixation mechanisms can be utilized to affix each of the deployment rods 14, 16, 18. In general, any suitable mechanism or method may be used to affix the deployment rods 14, 16, 18 to the implantable hernia prosthesis 12 in a removable and replaceable manner allowing the subsequent removal of the deployment rods 14, 16, 18 from the implantable hernia prosthesis 12. In illustrative embodiments, each of the deployment rods 14, 16, 18 are securely removably and replaceably affixed to the implantable hernia prosthesis 12 by one or more fastening mechanisms 32 (e.g., in the form of loops, stitches, slits, or the like). The fastening mechanisms 32 can be removable (e.g., by cutting, unstitching, unfastening, etc.), so as to facilitate the removal of the deployment rods 14, 16, 18. Alternatively and/or additionally, the deployment rods 14, 16, 18 can be slideable out from the fastening mechanisms 32. Additionally and/or alternatively to including the one or more fastening mechanisms 32, the deployment rods 14, 16, 18 can be affixed to the implantable hernia prosthesis 12 by glue or other adhesive(s), staple(s), tack(s), welding, sintering, or the like, so long as the fastening mechanism enables easy removal of the deployment rods 14,16,18 without damaging the prosthesis. As yet a further addition or alternative, the deployment rods 14, 16, 18 include barbs that protrude through the implantable hernia prosthesis 12 (e.g., through the mesh) and thereby fixedly maintain the deployment rods 14, 16, 18 to the implantable hernia prosthesis 12, as would be readily understood by those of skill in the art.

In illustrative embodiments, the fastening mechanisms 32 affixing the first deployment rod 14, the fastening mechanisms 32 affixing the second deployment rod 16, and the fastening mechanisms 32 affixing the third deployment rod 18 are all separately removable from the implantable hernia prosthesis 12. Accordingly, the fastening mechanisms 32 securing the first deployment rod 14 to the implantable hernia prosthesis 12 are enabled to be removed without also removing the fastening mechanisms 32 securing the second deployment rod 16 or the fastening mechanisms 32 securing the third deployment rod 18. Likewise, the fastening mechanisms securing the second deployment rod 16 to the implantable hernia prosthesis 12 are enabled to be removed without also removing the fastening mechanisms 32 securing the first deployment rod 14 or the fastening mechanisms 32 securing the third deployment rod 18. Similarly, the fastening mechanisms securing the third deployment rod 18 to the implantable hernia prosthesis 12 are enabled to be removed without also removing the fastening mechanisms 32 securing the first deployment rod 14 or the fastening mechanisms 32 securing the second deployment rod 16. In this way, the deployment rods 14, 16, 18 can be provided as separately removable from one another.

The deployment rods 14, 16, 18 can be of identical sizes and/or shapes or can have differing sizes and/or shapes. In general, each of the deployment rods 14, 16, 18 has a central longitudinal axis 15, 17, 19. In the example embodiment of FIGS. 1 and 2, the deployment rods 14, 16, 18 are more rigid than the implantable hernia prosthesis 12 (e.g., and thus can be substantially rigid relative to the flexible mesh sheet structure forming the implantable hernia prosthesis 12). As such, the deployment rods 14, 16, 18 can be configured to maintain the shape of the implantable hernia prosthesis 12 along the central longitudinal axes 15, 17, 19 of the deployment rods 14, 16, 18. The deployment rods 14, 16, 18 can be constructed of any suitable material enabling the deployment rods 14, 16, 18 to have a rigidity that is sufficiently high to support the weight of the implantable hernia prosthesis 12 during insertion, deployment, and placement of the implantable hernia prosthesis 12. For example, the deployment rods 14, 16, 18 each can be a wire rod formed of a medical grade metal. The particular size and shape of the deployment rods 14, 16, 18 similarly can be selected (in combination with the materials) to provide the desired rigidity.

Due to their shape and rigidity, the deployment rods 14, 16, 18 provide the implantable hernia prosthesis 12 with structural reinforcement and increased rigidity along only a single dimension of the implantable hernia prosthesis 12. In particular, the deployment rods 14, 16, 18 reinforce and rigidify along the axis of the width 22 of the implantable hernia prosthesis 12 in the rolled configuration, thereby causing the implantable hernia prosthesis 12 to exhibit greater resistance to bending along the axis of its width 22 when included in the system 10 in the rolled configuration than it would when used as a stand-alone device—without disrupting the natural or inherent flexibility along the axis of the length 20 of the implantable hernia prosthesis 12 when considered as a stand-alone device. As such, the system 10 exhibits greater resistance to bends along the axis of the width 22 of the implantable hernia prosthesis 12 than it does to bends along the axis of the length 20 of the implantable hernia prosthesis 12. Stated yet another way, in accordance with the example embodiments described herein, the deployment rods 14, 16, 18 effectively provide structural reinforcement in such a way as to rigidify the implantable hernia prosthesis 12 only in the transverse direction, and not in the longitudinal direction, as they have been illustrated in the corresponding figures. Accordingly, when included in the system 10 in the rolled configuration, the implantable hernia prosthesis 12 as a whole is capable of bending in a first direction (e.g., along its length 20, in the example embodiment of FIGS. 1 and 2) while simultaneously being hindered from bending in a second direction (e.g., along its width 22, in the example embodiment of FIGS. 1 and 2) that is perpendicular to the first direction. When rolled, the increased rigidity provided by the deployment rods 14, 16, 18 assists with insertion of the implantable hernia prosthesis 12 through the trocar cannula or incision. Furthermore, in some embodiments, the deployment rods 14, 16, 18 can have a relatively small diameter that does not significantly add to the thickness of the system 10. In this way, the total diameter of the system 10 when rolled can remain relatively small, as would be desired in some medical applications where smaller trocar cannulas and/or incisions are utilized.

Figure 3:
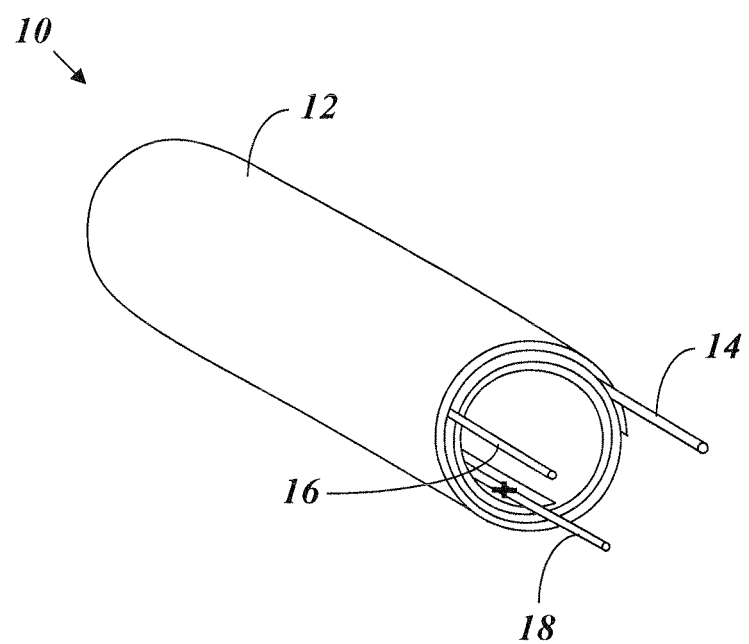
FIG. 3 is a perspective view of the system of FIG. 1, with the implantable hernia prosthesis in a rolled configuration for implantation, according to aspects of the present invention.
Figure 9:
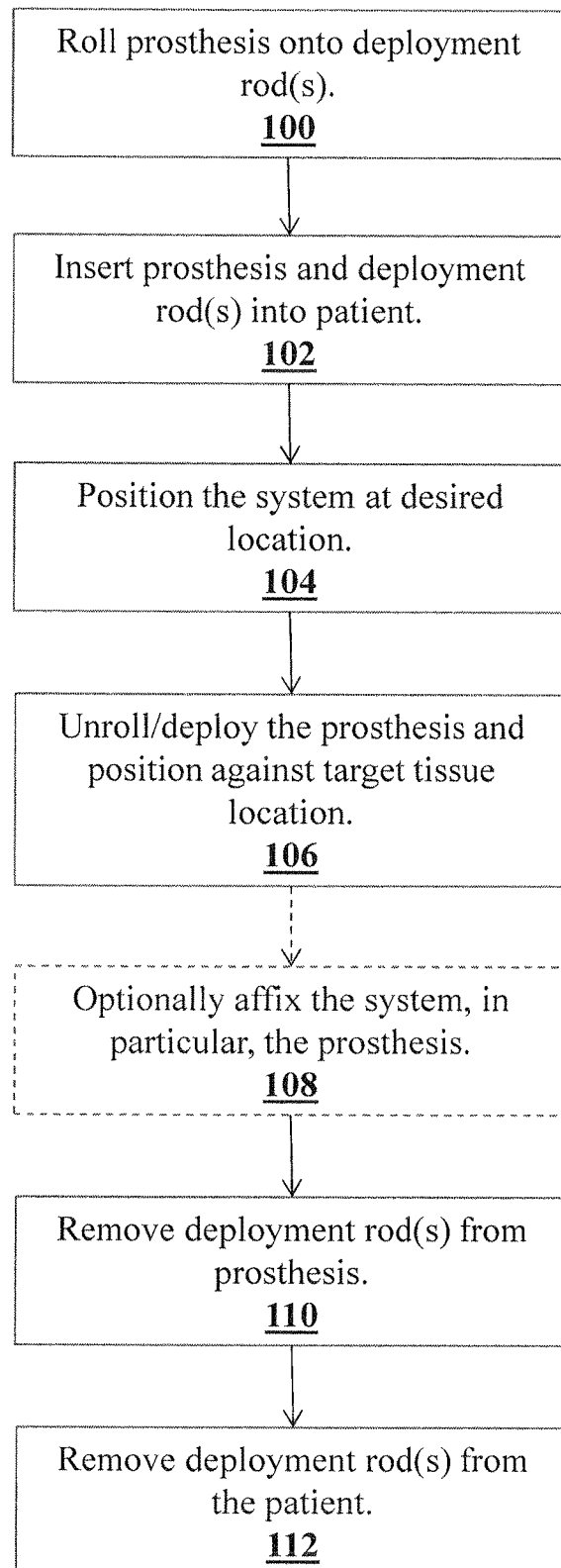
FIG. 9 is a flowchart illustrating a method of use of the system, according to one example embodiment of the present invention.

In operation (as shown in FIG. 9), the system 10 can be used in laparoscopic hernia repair, as would be appreciated by one of skill in the art upon reading the present specification. In particular, given that the natural flexibility of the length 20 of the implantable hernia prosthesis 12 is maintained even when included in the system 10, the system 10 can be rolled up (step 100) in a direction substantially orthogonal to the central longitudinal axes 15, 17, 19 (e.g., along the length 20 of the implantable hernia prosthesis 12 in the example embodiment of FIGS. 1 and 2) without bending (i.e., with at most very minimal or inconsequential bending) of the deployment rods 14, 16, 18. The step of rolling necessitates the previous placement of the deployment rods 14, 16, 18 in the prosthesis, which could occur at any time prior to rolling (e.g., at the point of manufacture, by the user just prior to rolling, or at any point in-between), such that it may or may not be a step prior to the step of rolling. As utilized herein, the phrase "without bending" refers to an overall requirement that the deployment rods of the present invention be essentially or substantially rigid, such that the provide structure to the system 10 that enables manipulation and placement of the prosthesis. As such, a rod that experiences minimal, inconsequential (to the desired function), bending would be considered to be a rod that performs "without bending" in accordance with the present invention, as would be appreciated by those skilled in the art. Once rolled in this way, the system 10 can be inserted into a patient, e.g., through one or more trocars (step 102). For example, FIG. 3 depicts the system 10 in such a rolled configuration (with the deployment rods 14, 16, 18 each unbent by the roll) prior to being implanted in a patient, in accordance with an example embodiment of the present invention. The rolled configuration of FIG. 3 can be produced by gripping the system 10 at the second end 26 of the length 20 of the implantable hernia prosthesis 12 and rolling the implantable hernia prosthesis 12 toward the first end 24 of the length 20 of the implantable hernia prosthesis 12 until all or substantially all of the length 20 of the implantable hernia prosthesis 12 is formed into a roll.

The system 10 is inserted into the body of a patient and advanced through one or more trocars to the site of the hernia defect (step 104), during which time a user can grip and manipulate the deployment rods 14, 16, 18 using graspers. For example, by gripping the deployment rods 14, 16, 18, a user can deploy (e.g., unroll) the system 10 and position the system 10 against the abdominal wall for fixation, as would be appreciated by one of skill in the art. In one illustrative embodiment, the system 10 is entirely unrolled by the user into the substantially flat configuration depicted in FIG. 1 and subsequently positioned against the defect site (step 106). Once adequately positioned, the system 10 can be affixed (step 108), e.g., using sutures and/or tacks, if desired (this step is optional depending on whether it is desirable or not to affix the prosthesis to the tissue). The deployment rods 14, 16, 18 then can be detached/removed from the implantable hernia prosthesis 12 (step 110) and removed from the patient (step 112), e.g., leaving behind only the affixed implantable hernia prosthesis 12.

Figure 4:
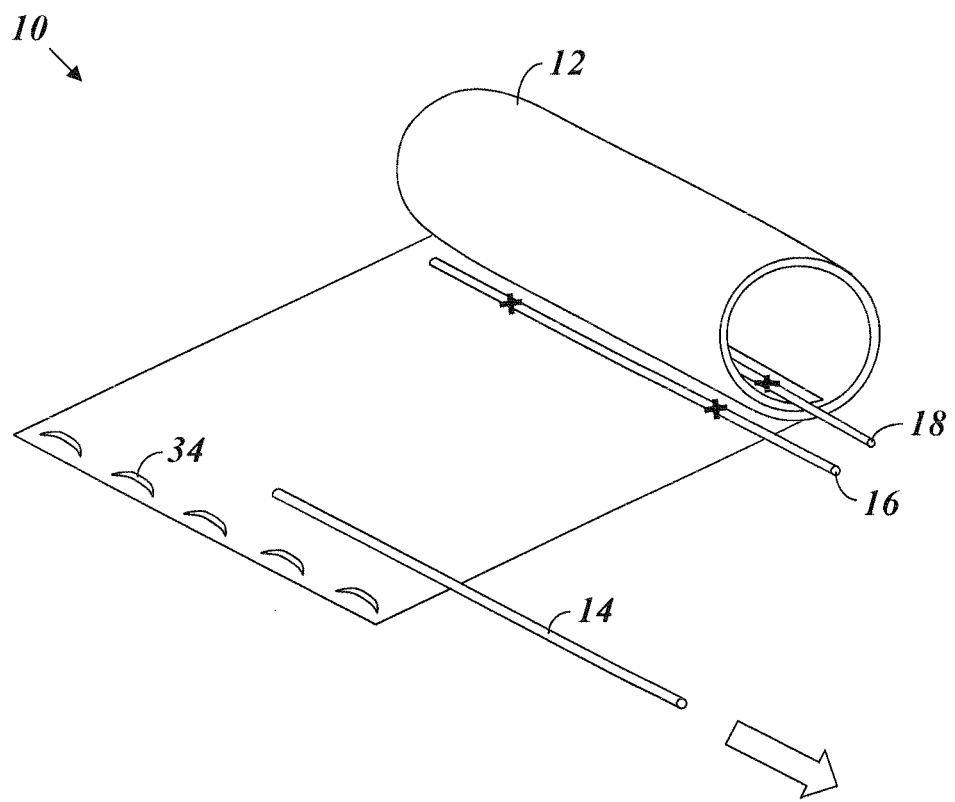
FIG. 4 is a perspective view of the system of FIG. 3 during deployment of the implantable hernia prosthesis, according to aspects of the present invention.

In an alternative illustrative embodiment of the present invention, the system 10 is deployed and affixed in a piecewise and step-by-step manner, e.g., by repeating a process of unrolling and affixing discrete portions of the implantable hernia prosthesis 12. In particular, and as depicted in FIG. 4, a portion of the system 10 can be unrolled, after which (a) the fastening mechanisms 32 coupling the first deployment rod 14 to the implantable hernia prosthesis 12 can optionally be removed and (b) the unrolled portion can be affixed to the surrounding tissue or muscle wall at the defect site. The unrolled portion can be affixed using one or more surgical sutures or tacks 34, as described previously herein. Next, subsequent to removing the fastening mechanisms 32 securing the first deployment rod 14, the first deployment rod 14 can be removed from the implantable hernia prosthesis 12. This process of affixing only a portion of the implantable hernia prosthesis 12 at a time can be repeated for remaining rolled portions of the implantable hernia prosthesis 12 (e.g., for those portions proximate the second and third deployment rods 16, 18). In particular, after removing the first deployment rod 14, a medial portion of the implantable hernia prosthesis 12 can be unrolled and affixed, and the second deployment rod 16 can be removed from the implantable hernia prosthesis 12. Subsequent to removing the second deployment rod 16, the remaining portion of the implantable hernia prosthesis 12 disposed at the second end 26 of the length 20 can be unrolled and affixed, and the third deployment rod 18 can be removed from the implantable hernia prosthesis 12. In this way, the implantable hernia prosthesis 12 can be inserted into a patient, placed appropriately at the target site using the deployment rods 14, 16, 18, and unrolled and affixed in a piecewise fashion using the deployment rods 14, 16, 18.

Figure 5:
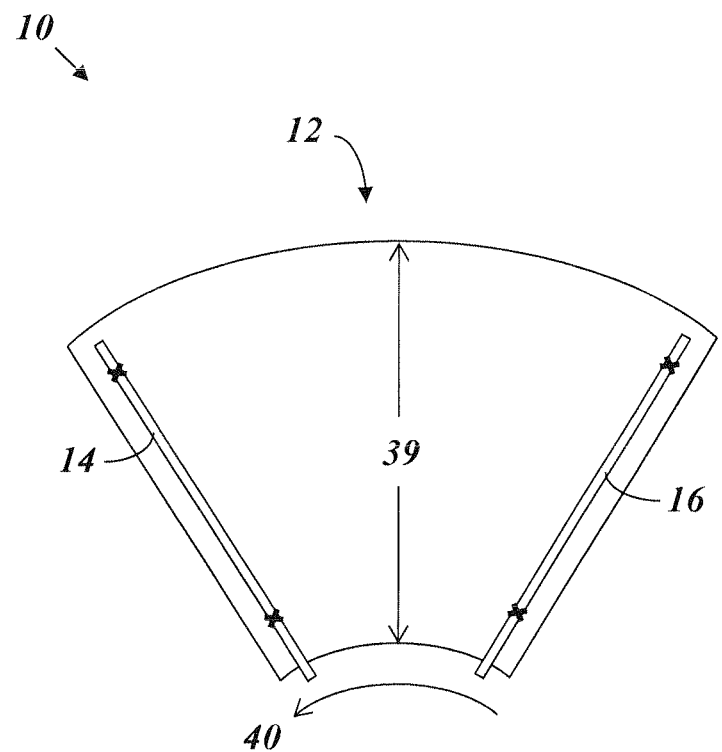
FIG. 5 is a top view of a prosthesis with two deployment rods removably coupled thereto, according to an example embodiment of the present invention.

Although three deployment rods 14, 16, 18 are illustrated in the example embodiment of FIGS. 1 through 4, it is alternatively contemplated that two, four, five, or more such deployment rods can be included in the system 10. For example, FIG. 5 depicts an embodiment of the system 10 in which only the first and second deployment rods 14, 16 are included. In the example embodiment of FIG. 5, the system 10 includes a prosthesis 12 that is formed of a single flexible, substantially arch or fan-shaped mesh sheet structure. As with the embodiment of FIGS. 1 and 2, the deployment rods 14, 16 of FIG. 5 are disposed across a majority of a dimension of the prosthesis 12. However, unlike the example embodiment of FIGS. 1 and 2, in the example embodiment of FIG. 5, each of the deployment rods 14, 16 is disposed across a majority of a radius 39 of the prosthesis 12. Furthermore, as with the example embodiment of FIG. 1, the system 10 according to the example embodiment of FIG. 5 is configured to be rolled in a direction substantially orthogonal to the central longitudinal axes 15, 17 of the deployment rods 14, 16 in such a way that all or substantially all of the prosthesis 12 (e.g., and thus all of the mesh sheet structure) forms one or more rolls without substantially or consequentially bending the deployment rods 14, 16. However, in the example embodiment of FIG. 5, the prosthesis 12 is configured to be rolled along in an angular direction 40, which is substantially orthogonal to the central longitudinal axes 15, 17 of the deployment rods 14, 16. As alluded to earlier herein, the deployment rods 14, 16, while not substantially parallel prior to the rolling operation, nonetheless result in a substantially parallel relative orientation to each other when in the rolled configuration. This has to do with curved shape of the prosthesis 12, as would be appreciated by those of skill in the art.

Figure 6:
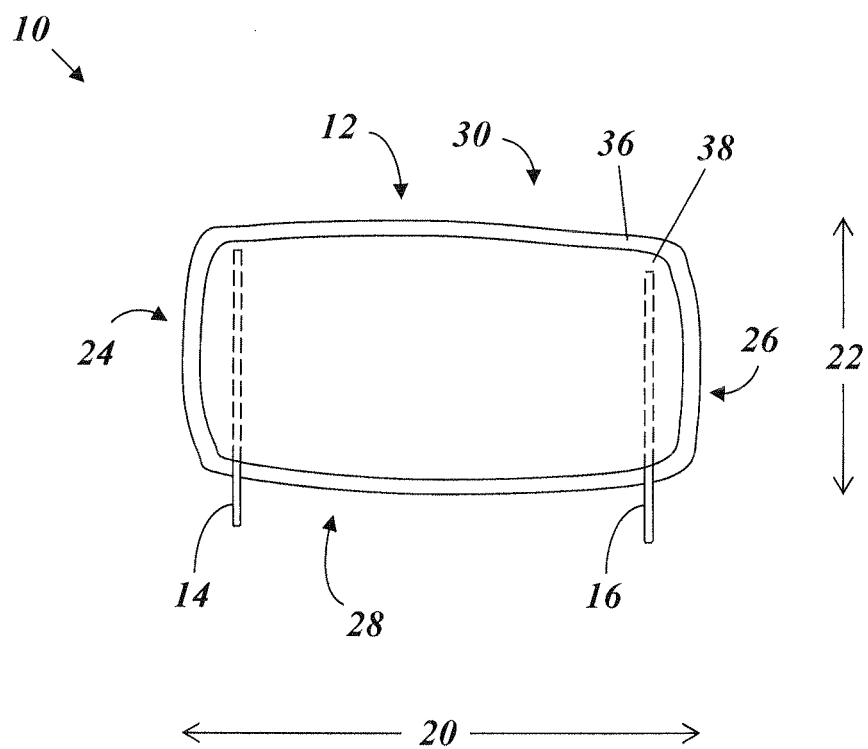
FIG. 6 is a top view of a prosthesis formed of two mesh sheet structures and having two deployment rods removably coupled thereto, according to an example embodiment of the present invention.

Although the implantable hernia prosthesis 12 of the example embodiments of FIGS. 1 through 5 include only a single mesh sheet structure forming only a single layer, the implantable hernia prosthesis 12 alternatively can include two or more mesh sheet structures forming multiple layers. For example, FIG. 6 depicts the system 10 in which the implantable hernia prosthesis 12 includes a first flexible mesh sheet structure 36 and a second flexible mesh sheet structure 38 coupled to the first flexible mesh sheet structure 36. As depicted, the first and second mesh sheet structures 36, 38 are coupled together near their outer peripheries. The second mesh sheet structure 38 is smaller in area than and substantially similar in shape to the first mesh sheet structure 36. However, in some alternative embodiments, the first and second mesh sheet structures 36, 38 are not similar in shape and/or size. The second mesh sheet structure 38 forms a layer on the first mesh sheet structure 36, and a pocket is formed between the first and second mesh sheet structures 36, 38. The first and second deployment rods 14, 16 are disposed within the pocket in such a way as to be removably coupled with the implantable hernia prosthesis 12. Accordingly, the pocket formed by the first and second mesh sheet structures 36, 38 is open at least at the positions where the first and second deployment rods 14, 16 enter the pocket. In the example embodiment of FIG. 6, the first and second deployment rods 14, 16 are disposed near the ends 24, 26 of the length 20 of the implantable hernia prosthesis 12, as illustrated.

Figure 7:
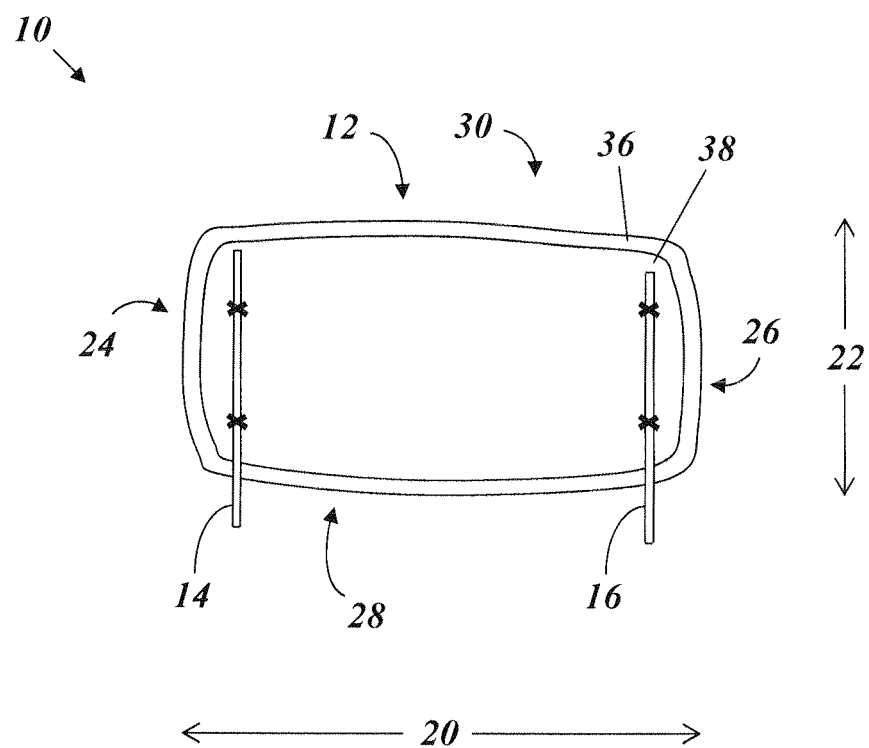
FIG. 7 is a top view of a prosthesis formed of two mesh sheet structures and having two deployment rods affixed at least to a first of the two mesh sheet structures, according to an example embodiment of the present invention.
Figure 8:
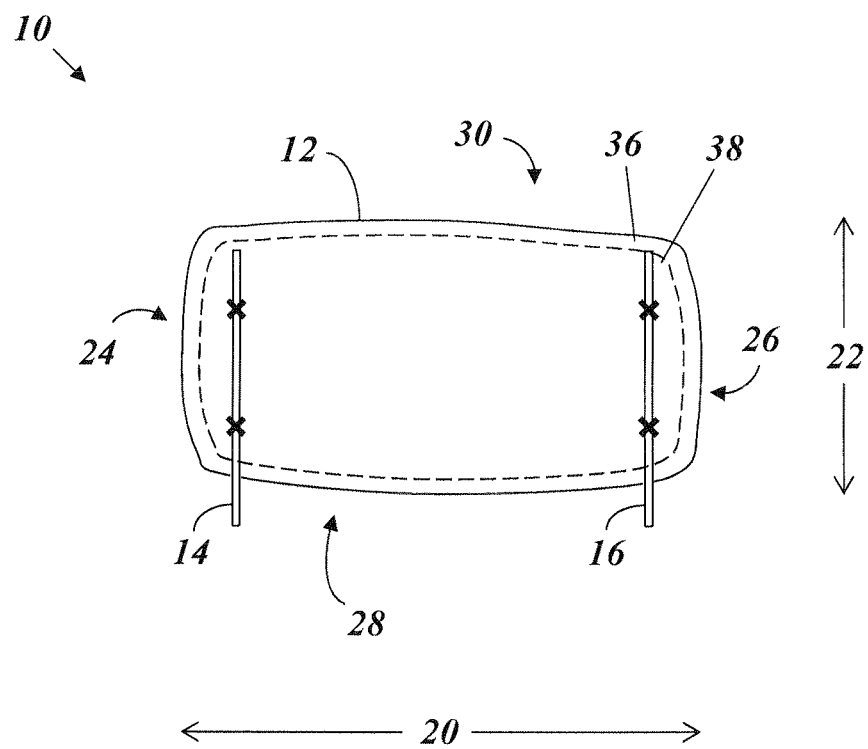
FIG. 8 is a top view of the prosthesis of FIG. 7, with the two deployment rods affixed at least to a second of the two mesh sheet structures, according to an example embodiment of the present invention.

In some embodiments, the implantable hernia prosthesis 12 includes the two or more mesh sheet structures forming stacked layers and the deployment rods 14, 16 are removably affixed to the implantable hernia prosthesis 12 by the one or more fastening mechanisms 32. For example, FIG. 7 depicts an embodiment according to the present invention, in which the deployment rods 14, 16 are affixed to the second mesh sheet structure 38. FIG. 8 depicts an embodiment according to the present invention, in which the deployment rods 14, 16 are affixed to the first mesh sheet structure 36. In some embodiments, the deployment rods 14, 16 are affixed to both the first mesh sheet structure 36 and the second mesh sheet structure 38 in such a way that the deployment rods 14, 16 and the fastening mechanisms 32 appear substantially as shown in FIG. 7 or FIG. 8 with the fastening mechanisms 32 instead passing through both the first and second mesh sheet structures 36, 38. In this way, in embodiments in which the implantable hernia prosthesis 12 includes two mesh sheet structures, the deployment rods 14, 16 generally can be coupled to the first mesh sheet structure 36, the second mesh sheet structure 38, or both.

Notably, the system 10 according to embodiments of the present invention provides a user with greater facility and ease of handling during operation. By providing two or more separate deployment rods 14, 16, 18 removably affixed to the implantable hernia prosthesis 12 in a substantially parallel arrangement, the system 10 permits users to roll the implantable hernia prosthesis 12 and separately control and manipulate various portions of the implantable hernia prosthesis 12. This has the beneficial effect of providing greater handling capabilities than known deployment devices presently utilized in the art with hernia patches. Furthermore, providing that the deployment rods 14, 16, 18 are separately removable allows a user to more easily work with discrete portions at a time, thereby reducing likelihood of tearing or rupturing unrolled portions, which remain protected in the rolled configuration (e.g., as illustrated in FIG. 4).

In addition, in accordance with embodiments of the present invention, the deployment rods 14, 16, 18 are configured to be manipulated independently of one another. Accordingly, the first deployment rod 14 (disposed at the first end 24 of the length 20 of the implantable hernia prosthesis 12) is provided with a range of motion, the passage within which does not inherently or necessarily effect motion of the second and/or third deployment rods 16, 18. Similarly, the third deployment rod 18 (disposed at the second end 26 of the length 20 of the implantable hernia prosthesis 12) is provided with a range of motion, wherein passage of the third deployment rod 18 within the range of motion does not inherently or necessarily effect motion of the first and/or second deployment rods 14, 16. This capability for some independent motion and control over the different deployment rods 14, 16, 18 provides a user with greater handling capabilities by enabling more focused control over smaller and more discrete portions of the implantable hernia prosthesis 12. Upon reading the present specification, one of skill in the art will appreciate yet further benefits not described herein.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A system, comprising:
   a prosthesis comprising a first flexible mesh sheet structure;
   two or more elongate rods each being removably coupled with the prosthesis and each being more rigid than the mesh sheet structure, in such a way that the combination of the two or more elongate rods with the mesh sheet structure rigidifies the mesh sheet structure along a length of each of the two or more elongate rods; and
   one or more fastening mechanisms mechanically coupling the two or more elongate rods to the first mesh sheet structure of the prosthesis,
   wherein the system is configured to be rolled in a direction substantially orthogonal to a central longitudinal axes of the two or more elongate rods in such a way that all or substantially all of the mesh sheet structure forms one or more rolls without bending the two or more elongate rods.

2. The system of claim 1, wherein the two or more elongate rods are separate and distinct from each other and two of the two or more elongate rods are independently moveable relative to each other.

3. The system of claim 1, wherein each one of the two or more elongate rods is slidable out of the one or more fastening mechanisms in a direction generally along the central longitudinal axis of that one of the two or more elongate rods.

4. The system of claim 1, wherein the one or more fastening mechanisms are configured to be cut to release the two or more elongate rods and are configured to be removed from the mesh sheet structure.

5. The system of claim 1, wherein the prosthesis further comprises a second flexible mesh sheet structure coupled to and forming a layer on the first mesh sheet structure.

6. The system of claim 5, wherein the two or more elongate rods are disposed between the first and second mesh sheet layers which removably couple the two or more elongate rods to the sheet in such a way that the two or more elongate rods are slidable out from between the first and second mesh sheet structures.

7. The system of claim 1, wherein the prosthesis further comprises a second flexible mesh sheet structure coupled to and forming a layer on the first mesh sheet structure, and wherein each of the two or more elongate rods are affixed to the first flexible mesh sheet structure, the second flexible mesh sheet structure, or both.

8. The system of claim 1, wherein at least one of the two or more elongate rods coupled to the prosthesis extends beyond and exterior to a perimeter edge of the prosthesis.

9. The system of claim 1, wherein at least one of the two or more elongate rods coupled to the prosthesis is graspable and maneuverable by a laparoscopic grasper or other separate tool.

10. The system of claim 1, wherein each of the two or more elongate rods extends across a majority of a dimension of the prosthesis.

11. The system of claim 1, wherein a first of the two or more elongate rods is disposed at a first end of the prosthesis and a second of the two or more elongate rods is disposed at a second end of the prosthesis, the second end of the prosthesis being opposite the first end.

12. The system of claim 11, wherein the two or more elongate rods further comprise a third rod disposed between the first and second rods at a central portion of the prosthesis.

13. The system of claim 1, wherein the two or more elongate rods have a rigidity suitable for using the two or more elongate rods to manipulate and position the prosthesis at a target site.

14. The system of claim 1, wherein each of the two or more elongate rods comprises a wire rod or a plastic rod.

15. A method for deploying a mesh prosthesis using a system comprising a prosthesis comprising a first flexible mesh sheet structure, and two or more elongate rods, wherein each rod is removably coupled with the first mesh sheet structure of the prosthesis by one or more fastening mechanisms, and each rod is more rigid than the first mesh sheet structure in such a way that the combination of the two or more elongate rods mechanically coupled with the first mesh sheet structure rigidifies the first mesh sheet structure along a length of each of the two or more elongate rods, the method comprising:
providing a rolled prosthesis in which, using the two or more elongate rods, the prosthesis is rolled in a direction substantially orthogonal to a central longitudinal axes of the two or more elongate rods in such a way that all or substantially all of the first mesh sheet structure forms one or more rolls without bending the two or more elongate rods;
inserting the rolled prosthesis into a bodily cavity;
unrolling the prosthesis, using the two or more elongate rods; and
removing the two or more elongate rods from the unrolled prosthesis.

16. The method of claim 15, wherein the two or more elongate rods are separate and distinct from each other and two of the two or more elongate rods are independently moveable relative to each other.

17. The method of claim 15, wherein removing the two or more elongate rods comprises sliding the two or more elongate rods out of the one or more fastening mechanisms in a direction generally along the central longitudinal axis of each respective rod of the two or more elongate rods.

18. The method of claim 15, wherein the prosthesis further comprises a second flexible mesh sheet structure coupled to and forming a layer on the first mesh sheet structure.

19. The method of claim 18, wherein the two or more elongate rods are disposed between the first and second mesh sheet layers which removably couple the two or more elongate rods to the sheet in such a way that the step of removing the two or more elongate rods comprises sliding the two or more elongate rods out from between the first and second mesh sheet structures.

20. The method of claim 15, wherein at least one of the two or more elongate rods coupled to the prosthesis extends beyond and exterior to a perimeter edge of the prosthesis.

21. The method of claim 15, wherein at least one of the two or more elongate rods coupled to the prosthesis is graspable and maneuverable by a laparoscopic grasper or other separate tool.

22. The method of claim 15, wherein the two or more elongate rods have a rigidity suitable for using the two or more elongate rods to manipulate and position the prosthesis at a target site, further comprising manipulating and positioning the prosthesis at the target site using the two or more elongate rods.

23. The method of claim 15, wherein the step of providing the rolled prosthesis comprises the prosthesis being rolled at a point of manufacture.

24. The method of claim 15, wherein the step of providing the rolled prosthesis comprises a user using the two or more elongate rods to roll the prosthesis in a direction substantially orthogonal to the central longitudinal axes of the two or more elongate rods in such a way that all or substantially all of the mesh sheet structure forms one or more rolls without bending the two or more elongate rods and prior to the user inserting the prosthesis into a bodily cavity.

25. A system, comprising:
a prosthesis comprising a flexible mesh sheet structure; and
two or more elongate rods each being removably coupled with the prosthesis and each being more rigid than the mesh sheet structure, in such a way that the combination of the two or more elongate rods with the mesh sheet structure rigidifies the mesh sheet structure along a length of each of the two or more elongate rods;
wherein the system is rolled in a single direction substantially orthogonal to a central longitudinal axes of the two or more elongate rods in such a way that all or substantially all of the mesh sheet structure forms a roll having a plurality of layers with two of the two or more elongate rods disposed between layers of the roll; and
wherein the two or more elongate rods are separate and distinct from each other and two of the two or more elongate rods are independently moveable relative to each other.

26. A system, comprising:
a prosthesis comprising a flexible mesh sheet structure; and
two or more elongate rods, each rod removably coupled with the prosthesis by one or more fastening mechanisms selected from the group consisting of loops, stitches and slits, and each rod is more rigid than the mesh sheet structure, in such a way that the combination of the two or more elongate rods with the mesh sheet structure rigidifies the mesh sheet structure along a length of each of the two or more elongate rods;
wherein the system is configured to be rolled in a direction substantially orthogonal to a central longitudinal axes of the two or more elongate rods in such a way that all or substantially all of the mesh sheet structure forms one or more rolls;
wherein the two or more elongate rods are separate and distinct from each other and two of the two or more elongate rods are independently moveable relative to each other; and
wherein the two or more elongate rods have sufficient rigidity to enable use of the two or more elongate rods to manipulate and position the prosthesis at a target site.

* * * * *